US012589183B2

(12) United States Patent
Teng et al.

(10) Patent No.: US 12,589,183 B2
(45) Date of Patent: Mar. 31, 2026

(54) HEMOSTATIC PASTE AND USES THEREOF

(71) Applicant: Guangzhou Bioseal Biotech Co., Ltd., Guangzhou Science City (CN)

(72) Inventors: Ling Teng, Guangzhou Science City (CN); Tingwan Xie, Guangzhou Science City (CN); Yuan Tian, Guangzhou Science City (CN); Dengmin Feng, Guangzhou Science City (CN); Peiqiu Wang, Guangzhou Science City (CN)

(73) Assignee: Guangzhou Bioseal Biotech Co., Ltd., Guangzhou Science City (CN)

( * ) Notice: Subject to any disclaimer, the term of this patent is extended or adjusted under 35 U.S.C. 154(b) by 869 days.

(21) Appl. No.: 17/781,075

(22) PCT Filed: Dec. 25, 2019

(86) PCT No.: PCT/CN2019/128204
§ 371 (c)(1),
(2) Date: May 31, 2022

(87) PCT Pub. No.: WO2021/128050
PCT Pub. Date: Jul. 1, 2021

(65) Prior Publication Data
US 2023/0001048 A1 Jan. 5, 2023

(51) Int. Cl.
| A61L 24/00 | (2006.01) |
| A61L 24/08 | (2006.01) |
| A61L 26/00 | (2006.01) |
| C08L 3/04 | (2006.01) |
| C08L 5/08 | (2006.01) |
| C08L 71/02 | (2006.01) |

(52) U.S. Cl.
CPC ......... *A61L 26/0052* (2013.01); *A61L 26/008* (2013.01); *C08L 3/04* (2013.01); *C08L 5/08* (2013.01); *C08L 71/02* (2013.01); *A61L 2400/04* (2013.01); *C08L 2312/00* (2013.01)

(58) Field of Classification Search
None
See application file for complete search history.

(56) References Cited

U.S. PATENT DOCUMENTS

| 8,105,622 B2 | 1/2012 | Sawhney |
| 2008/0226688 A1 | 9/2008 | Depaula |

| 2009/0062233 A1 | 3/2009 | Ji et al. |
| 2012/0027817 A1 | 2/2012 | Kronenthal |
| 2013/0090291 A1* | 4/2013 | Gulle .................... A61K 35/32 514/13.7 |
| 2013/0261192 A1 | 10/2013 | Yang et al. |
| 2014/0213688 A1 | 7/2014 | Bezwada et al. |

FOREIGN PATENT DOCUMENTS

| CA | 2121028 A1 | 4/1993 |
| CN | 103957948 A | 7/2014 |
| CN | 104349797 A | 2/2015 |
| CN | 104623720 A | 5/2015 |
| CN | 104623740 A | 5/2015 |
| CN | 105536039 A | 5/2016 |
| CN | 107115557 A | 9/2017 |
| CN | 107158452 A | 9/2017 |
| WO | 2007128926 A1 | 11/2007 |
| WO | 2018075866 A1 | 4/2018 |
| WO | 2019137414 A1 | 7/2019 |

OTHER PUBLICATIONS

Capanema, et al., Superabsorbent crosslinked carboxymethyl cellulose-PEG hydrogels for potential wound dressing applications, International Journal of Biological Macromolecules, vol. 106, pp. 1218-1234, 2018.
International Search Report and Written Opinion, PCT/CN2019/128204, Sep. 25, 202, pp. 1-14.
"Standard Test Method for Strength Properties of Tissue Adhesives in T-Peel by Tension Loading", ASTM International, Designation: F2256—05, 2 pages, 2015.
Omidian et al., "Swelling and Crosslink Density Measurements for Hydrogels", Iranian Journal of Polymer Science and Technology, vol. 3, No. 2, pp. 115-119, 1994.

* cited by examiner

*Primary Examiner* — Brian Gulledge
(74) *Attorney, Agent, or Firm* — David R. Crichton

(57) ABSTRACT

Disclosed herein is a non-flowable and deformable hemostatic compositions comprised of a xerogel crosslinked powdered polysaccharide dispersed within a substantially anhydrous blend of: glycerol, and polyethylene glycol (PEG), wherein the PEG and glycerol are present in a ratio ranging from higher than 1:1.3: to below 1:2.7 by weight, respectively, and wherein the powder content in the composition is above 50%, by weight. Methods of making the non-flowable compositions, and uses of the compositions in methods for treating a wound or a bleeding tissue, such as bone tissue, are further disclosed.

17 Claims, 6 Drawing Sheets

HEMOSTATIC PASTE AND USES THEREOF

CROSS-REFERENCE TO RELATED APPLICATIONS

This application is a national phase entry of International Application No. PCT/CN2019/128204, filed on Dec. 25, 2019, which is incorporated herein in its entirety.

FIELD OF THE INVENTION

The present invention relates, inter alia, to non-flowable and deformable compositions, methods of making thereof, and using same for treating bleeding tissues.

BACKGROUND OF THE INVENTION

In a wide variety of circumstances, animals, including humans, can suffer from bleeding due to wounds such as bone wounds or during surgical procedures. In some circumstances, the bleeding is relatively minor, and normal blood clotting functions, in addition to the application of simple first aid, is all that is required. In other circumstances, substantial bleeding can occur. These situations usually require specialized equipment and materials as well as personnel trained to administer appropriate aid.

Bleeding during surgical procedures may manifest in many forms. It can be discrete or diffuse from a large surface area. It can be from large or small vessels, arterial (high pressure) or venous (low pressure) of high or low volume. It may be easily accessible or it may originate from difficult to access sites. The control of bleeding is essential and critical in surgical procedures to minimize blood loss, to reduce post-surgical complications, and to shorten the duration of the surgery in the operating room. The selection of appropriate methods or products for the control of bleeding is dependent upon many factors, which include, but are not limited to, bleeding severity, anatomical location of the source and the proximity of adjacent critical structures, whether the bleeding is from a discrete source or from a broader surface area, visibility and precise identification of the source and access to the source.

Conventional methods to achieve hemostasis include use of surgical techniques, sutures, ligatures or clips, and energy-based coagulation or cauterization. When these conventional measures are ineffective or impractical, adjunctive hemostasis techniques and products are typically utilized.

To address the above-described problems, materials have been developed for controlling excessive bleeding or as adjuncts to hemostasis. Topical Absorbable Hemostats (TAHs) are widely used in surgical applications. TAHs encompass products in various forms, such as based on woven or non-woven fabrics or sponges, and are typically made of at least partially resorbable materials, ranging from natural to synthetic polymers and combinations thereof, including lactide-glycolide based co-polymers such as polyglactin 910, oxidized cellulose, oxidized regenerated cellulose (ORC), gelatin, collagen, chitin, chitosan, starch etc. Gelatin is used in various forms with or without a topical thrombin solution. Also, widely used are biologically active topical hemostatic products (topical thrombin solutions, fibrin sealants, etc.) and a variety of synthetic topical sealants.

To improve the hemostatic performance, scaffolds based on the above mentioned TAH materials can be combined with biologically-derived clotting factors, such as thrombin and fibrinogen.

Fibrin sealants, also known as fibrin glues, have been in use in the clinic for decades. Oftentimes, fibrin sealant comprises two liquid components, a fibrinogen comprising component and a thrombin comprising component, which are stored frozen due to their inherent instability. Sometimes fibrin sealant products comprise two freeze dried components, which require reconstitution immediately prior to use and delivery by a conjoined syringe or other double-barreled delivery device. Freeze dried formulations are typically stable, but the fibrinogen component is difficult to reconstitute. Many hemostatic formulations currently available on the market or in development utilize lyophilized fibrinogen, frequently in combination with lyophilized thrombin, with hemostatic formulations applied in the form of dry powder, semi-liquid paste, liquid formulation, or optionally disposed on a supporting scaffold such as absorbable fabric scaffold.

Hydrogels are materials that absorb solvents (such as water), undergo rapid swelling without discernible dissolution, and maintain three-dimensional networks capable of reversible deformation.

To provide dressings with enhanced hemostatic and tissue sealing and adhering properties, therapeutic agents, including, but not limited to, thrombin, fibrin and fibrinogen have been combined with dressing carriers or substrates, including gelatin-based carriers, polysaccharide-based carriers, glycolic acid or lactic acid-based carriers and a collagen matrix.

US Patent Application having a publication No. 2013/0261192 discloses a medical absorbable hemostatic and wound healing promoting material for bone wounds and a preparation method thereof. The absorbable hemostatic material for bone wounds is formed of 40-95% of a base material and 5-60% of an adjuvant, based on weight percent, wherein the base material is an oligosaccharide, a polysaccharide, or a mixture of the oligosaccharide and the polysaccharide, and the adjuvant includes (1) one or more polyhydric alcohols. (2) one or more vegetable oils, and (3) one or more emulsifying agents.

US Patent Application having a publication No. 2012/0027817 relates to mechanically hemostatic body-absorbable compositions having a putty-like consistency comprising a finely powdered polysaccharide and a biocompatible liquid comprising one or more block copolymers of ethylene oxide and propylene oxide.

U.S. Pat. No. 8,105,622 relates to pharmaceutically acceptable hydrogel polymers of natural, recombinant or synthetic origin, or hybrids thereof, introduced in a dry, less hydrated, or substantially deswollen state and rehydrate in a physiological environment to undergo a volumetric expansion and to affect sealing, plugging, or augmentation of tissue, defects in tissue, or of organs.

High bleeding volume and transfusion rate are major challenges during the orthopedic procedures. Energy devices like monopolar are rather designed for soft tissues, while bone waxes are generally not absorbable by the body.

There is a need in improved hemostatic forms and materials which facilitate ease of application and rapid onset of hemostasis for wounds such as bone wounds.

SUMMARY OF THE INVENTION

The present invention relates, inter alia, to non-flowable and deformable compositions, methods of making thereof, and using same for treating bleeding tissues.

Currently, hemostatic methods used, especially in orthopedic surgeries, are limited. The bone wax is the most common used material, but it is non-absorbable/degradable. This might lead to several problems, including impediment of bone regeneration and infections. Energy devices like monopolar are also used in orthopedic surgeries, but these devices are less effective on bone tissues.

The disclosed composition can be used is effective, safe, as well as bio-degradable hemostat for the human body.

According to an aspect of the present disclosure, there is provided a non-flowable and deformable hemostatic composition comprising: a xerogel crosslinked powdered polysaccharide dispersed within a substantially anhydrous blend of: glycerol, and polyethylene glycol (PEG), optionally, wherein the PEG and glycerol are present in a ratio between higher than 1:1.3 to below 1:2.7, by weight, respectively, and wherein the powder content in the composition is at least 50% by weight.

In some embodiments, the polysaccharide comprises a polymer selected from the group consisting of: carboxymethyl starch (CMS), hyaluronic acid (HA), and a mixture, derivative, or a copolymer thereof.

In some embodiments, the PEG comprises PEG 400.

In some embodiments, the xerogel crosslinked powdered polysaccharide is milled.

In some embodiments, the crosslinked polysaccharide is crosslinked via a polyfunctional carboxylic acid, wherein typically the acid is selected from malic acid, tartaric acid, citric acid, malonic acid, succinic acid, glutaric acid, adipic acid, and any mixture thereof.

In exemplary embodiments, the acid comprises citric acid.

In some embodiments, the cross-linked CMS is in the form of suspended powder having median particle size of less than 100 microns.

In some embodiments, the composition comprises less than 5%, optionally less than 3%, or less than 1%, by weight, of water.

In some embodiments, the glycerol is present at a concentration of 15 to 30%, and/or the PEG is present at a concentration of 10 to 25%, by weight.

In some embodiments, the xerogel crosslinked powdered polysaccharide has a swelling capacity in water of at least 10 times, of its weight at 25° C., optionally within less than 2 min.

In some embodiments, the xerogel crosslinked powdered polysaccharide features a degradation rate of 60% to 80%, by initial weight, in vivo.

In some embodiments, the composition is substantially devoid of polypropylene glycol.

In some embodiments, the composition is characterized by minimum bond strength ranging from 3.5 to 4.5 N/m as measured e.g., by T-peel test according to ASTM F2256-052015.

In some embodiments, the composition is in the form of paste.

In some embodiments, the composition is characterized as being non sticky to nitrile, e.g., nitrile gloves.

In some embodiments, the composition has a crosslinking degree (ρ) of about crosslinking degree (ρ) of 0.0047 to 0.0054 mol/ml.

In some embodiments, the composition is devoid of any supporting substrate or sheet.

According to another aspect of the present disclosure, there is method of making a non-flowable composition comprising the steps of: providing a xerogel crosslinked powdered polysaccharide; adding to the xerogel anhydrous blend of: glycerol, and PEG, wherein the PEG and glycerol are present in a ratio between higher than 1:1.3 to below 1:2.7, by weight, respectively, and wherein the powder content in the composition is above 60% by weight; and mixing the blend to form said non-flowable composition. In some embodiments, there is provided a sealant layer obtained by the method.

According to another aspect of the present disclosure, there is provided a method of making a wound dressing containing the disclosed composition in an embodiment thereof, comprising a step of applying the composition onto at least one face of a flexible bioabsorbable sheet substrate.

According to another aspect of the present disclosure, there is provided a use of the disclosed composition in an embodiment thereof in a method for treating a wound or a bleeding tissue, the method comprising applying the disclosed composition in any embodiment thereof to a or bleeding tissue.

In some embodiments, the bleeding tissue is a bone tissue. In some embodiments, the method is an orthopedic or spinal surgery.

According to another aspect of the present disclosure, there is provided a kit comprising: a container containing the disclosed composition in an embodiment thereof; an applicator for applying the composition to a tissue; and optionally instructions for use.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

US 12,589,183 B2

5

Figure 5:
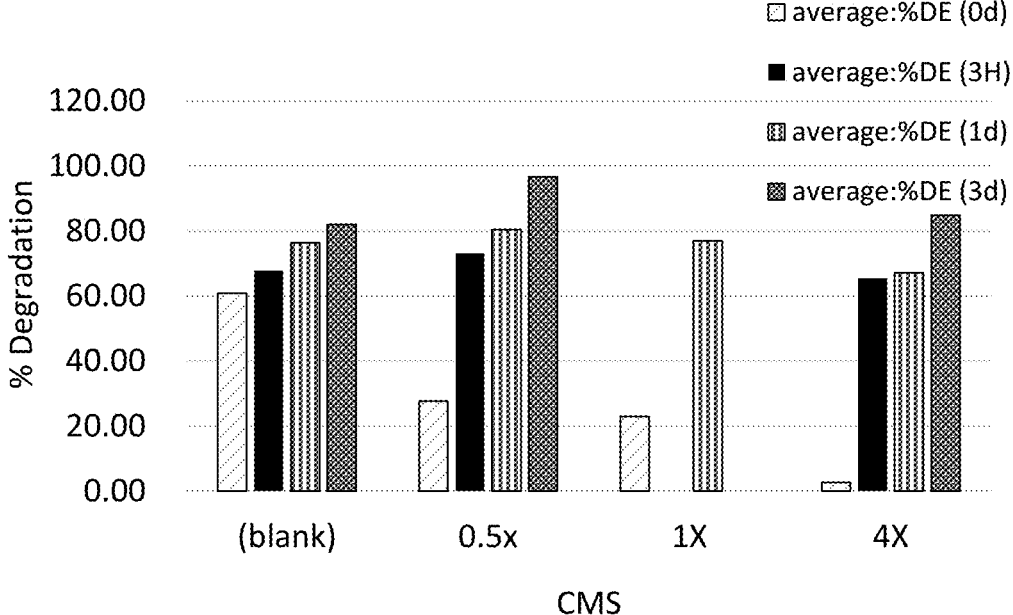
Figure 6A:
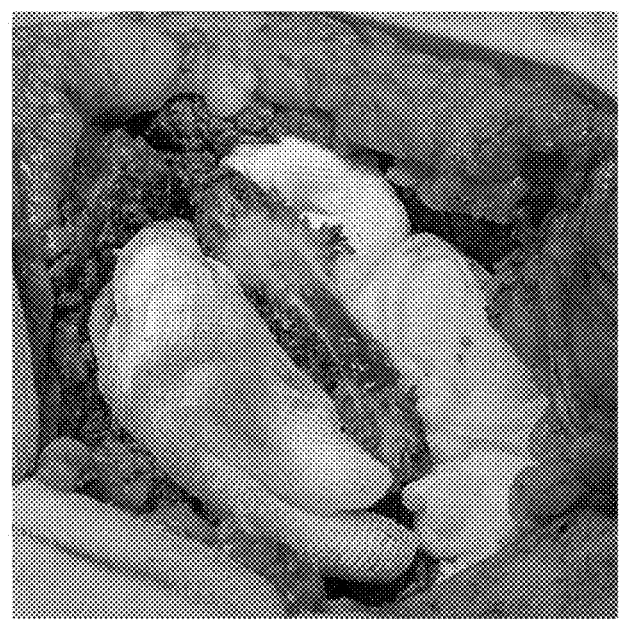
Figure 6B:
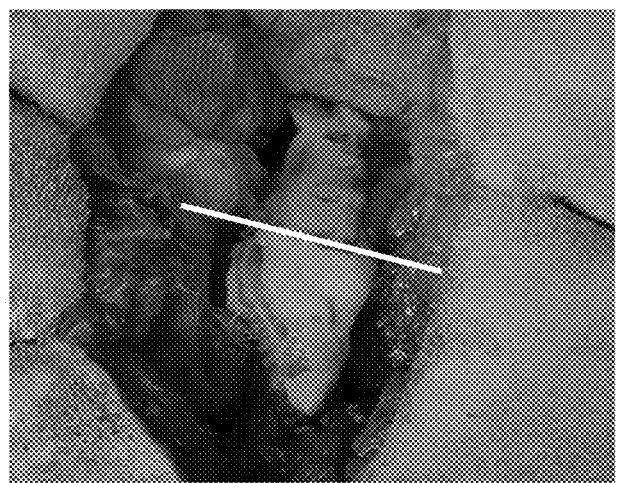
Figure 7:
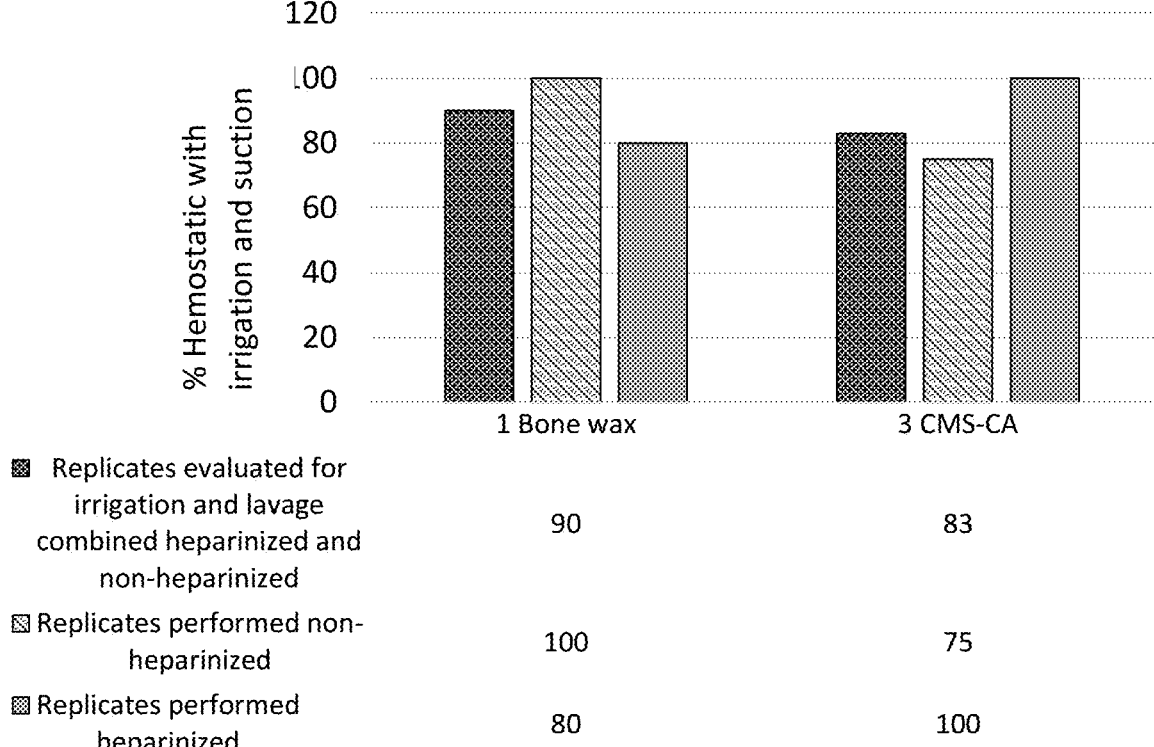

FIG. 5 presents a bar graph showing the degradation (DE) rate (%) of CMS-CA samples with different crosslinking rate according to Table 7; average of 3 tested samples for each;

FIGS. 6A-B present photographic images hemostasis evaluation on sheep ilium defect model: the defect was created, and no treatment was applied during 10 min to ensure the hemostasis was not due to auto coagulation (FIG. 6A); Bone wax (above the marked line) and CMS-CA (below the marked line) were applied to the same defect surface to evaluate acute hemostasis, durable hemostasis, and adhesiveness (FIG. 6B); and FIG. 7 presents a bar graph showing combined results of % hemostasis (with irrigation and suction) for CMS-CA and control (bone wax) according to Table 15; CMS-CA shown similar performance compared to bone wax.

DETAILED DESCRIPTION

The present invention relates, inter alia, to non-flowable and deformable compositions, and to methods for manufacturing and using such composition e.g. to reduce bleeding, sealing and/or desired adhesiveness e.g., in bone tissues.

The compositions may be used for promoting hemostasis and tissue sealing and, more particularly, to fast swelling, highly absorbent hemostatic composition in the form of a non-flowable paste comprising a mixture of crosslinked polysaccharide with one or more dispersants. Once contact with moisture (blood), the dry particles absorb water very fast and swell, allowing to fill the micro-structure or cavities of e.g., a bone tissue, to achieve hemostasis.

In one aspect, there is provided a non-flowable and deformable hemostatic composition comprising a xerogel comprising crosslinked powdered polysaccharide dispersed within a substantially anhydrous blend of one or more dispersants. The xerogel comprising crosslinked powdered polysaccharide is referred to as: "xerogel crosslinked powdered polysaccharide".

In some embodiments, the polysaccharide comprises a polymer selected from carboxymethyl starch (CMS), hyaluronate, and a mixture, copolymer or a derivative thereof.

Within the context of the present invention, the term "derivative", when used in connection with polysaccharide, refers to polysaccharide that is derived from the natural polysaccharide by chemical modification such as etherification or esterification.

Hereinthroughout, for each one of "PEG", "CMS", "HA", and "glycerol" it is also meant to encompass any derivative thereof.

Starch is a polymeric carbohydrate comprising numerous glucose units joined by glycosidic bonds. This polysaccharide is produced by most green plants as energy storage. CMS is one of the major varieties of modified starch, starch ethers genus, is a water-soluble anionic polymer compound. It is commonly used sodium salt, also known as CMS-Na, wherein a white or yellow powder, odorless, tasteless, non-toxic, and may absorb moisture.

As used herein, the term "hyaluronic acid" or "HA" means hyaluronate, or any salt thereof, e.g., sodium hyaluronate. Also, the term "HA derivative", when used herein, is intended to encompass, inter alia, any salt thereof, in particular the sodium salt of the HA derivative.

The term "hyaluronic acid" encompasses all variants and combinations of variants of hyaluronic acid, or hyaluronan, of various chain lengths and charge states, as well as various chemical modifications. That is, the term also encompasses the various hyaluronate salts of hyaluronic acid, such as sodium hyaluronate. Various modifications of the hyaluronic acid are therefore encompassed by the term, such as oxidation, e.g. oxidation of $CH_2OH$ groups to COOH; periodate oxidation of vicinal hydroxyl groups, optionally followed by reduction or imine formation; reduction, e.g., reduction of COOH to $CH_2OH$; sulphation; deamidation, optionally followed by deamination or amide formation with new acids; esterification; substitutions with various compounds, e.g., using a cross-linking agent as described herein.

According to one embodiment, a fast swelling, superabsorbable, biodegradable hemostatic composition comprises: carboxymethyl starch (CMS) crosslinked by citric acid (or similar polyfunctional carboxylic acid e.g., malic, tartaric, citric, malonic, succinic, glutaric, or adipic acid) above 50% by weight, which is suspended or dispersed as a fine powder, as demonstrated in the Examples section, in a mixture of a first non-toxic glycerol-containing and hygroscopic dispersant, and a second non-toxic, optionally alcohol-functionalized, dispersant, which in some embodiments comprises polyethylene glycol (PEG). The hemostatic composition of the invention is pasty and/or dough-like, non-flowable, and has sufficient viscosity and cohesion to maintain a continuous, singular form at room temperature when placed upon flat, unconstrained flat surfaces and within cavities or voids. The inventive composition is substantially free of water or anhydrous. In some embodiments, both dispersants are hydrophilic. Hereinthroughout, cross-linked hyaluronate may be used instead of, or in addition to, crosslinked CMS xerogel.

Typically, the dried polysaccharide xerogel has three-dimensional crosslinked polymeric network that are capable of absorbing large quantities of water, saline or physiological liquid forming hydrogels. The powerful osmotic action dehydrates and gels the blood component upon contact, and swelling to more than 20 times of the dry xerogel weight or volume may be achieved to fill up a wound and produce a "back pressure" in the confined wound space to simulate tamponade effect or enhance the natural clotting process in internal voids. These dispersants (e.g., PEG and glycerol) maintain the anhydrous environment and makes the composition hygroscopic.

In another embodiment, the instantly disclosed composition (e.g., in the form of hemostatic paste) can be employed for a timed or delayed release of active agents e.g. as a drug-delivery vehicle. The composition may incorporate growth factors, antibiotics, local anesthetics, and any agents useful to improve wound healing, prevent infection or relieve pain. By incorporating coagulation activators, platelet activators or blood vessel constrictors, fibrinolytic function inhibitors, etc., including e.g., thrombin, fibrinogen, the hemostatic effect of the paste may be further improved.

In some embodiments, the main component of the paste/dough-like forming the xerogel is polysaccharide crosslinked by citric acid, having an increased mechanical stability. Several polysaccharides showed high absorption ability in the unmodified state, but these have the disadvantage that the swelling occurs only in warm water and that dissolution can take place. Such unmodified/uncross-linked polysaccharides have low mechanical stability and can undergo degradation, and/or retrogradation, and/or and syneresis (contraction of a gel accompanied by the separating out of liquid).

In some embodiments, the xerogel comprises (crosslinked) polysaccharide selected from CMS or HA hyaluronate In some embodiments, one of the dispersants comprises glycerol. In some embodiments, the dispersants comprise glycerol, and polyethylene glycol (PEG).

In some embodiments, the glycerol and polyethylene glycol (PEG), are present in a weight ratio ranging from 1:2.7 to 2.7:1, or 1.3:1 to 2.7:1, respectively. In some embodiments, the glycerol and polyethylene glycol (PEG), are present in a weight ratio of above 1.3:1 to less than 2.7:1, respectively. In some embodiments, the glycerol and polyethylene glycol (PEG), are present in a weight ratio of 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1 or approaching 2.7:1, respectively, including any value and range therebetween. In some embodiments, the glycerol and polyethylene glycol (PEG), are present in a ratio between higher than 1.3:1 to below 2.7:1 by weight, respectively. Reference is made in this respect to FIGS. 4A-D, showing that when the ratio was about 1:1.3, the sample was dry and easy to crack during kneading by hand. When the ratios are 1:1.7 and 1:2.2, the samples were easy to deform by kneading. It is suggested that these ratios are the appropriate PEG to glycerol range. When the ratio increased to about 1:2.7, the sample was too thin, somehow flowable, and was very sticky to nitrile gloves, that is being less effective for practical use by a surgeon for placing the paste over the bleeding site. These ratios, on the other hand, still satisfy a desired adhesiveness range of 2.5 to 4 N/m e.g., at least 3 N/m, as tested using a T-peel test (see FIG. 2 and Tables 5 and 6).

In some embodiments, the powder content in the composition is above 50%, by weight. In some embodiments, the powder content in the composition is above 60%, by weight. In some embodiments, the powder content in the composition is about 50% to 70%, by weight. In some embodiments, the powder content in the composition is about 50%, about 55%, about 60%, about 65%, or about 70%, by weight, including any value and range therebetween.

The term "PEG" means polyethylene glycol, a polymer with the structure ($-CH_2CH_2O-$)$_n$ that is synthesized normally by ring opening polymerization of ethylene oxide. The term "PEG-400", as used herein, refers to a polymeric form of ethylene glycol, i.e. polyethylene glycol, which has an average molecular weight of about 400 (e.g., 360 to 440) grams/mole, termed "PEG 400".

The term "deformable" generally refers to any structure that may deform in response to an external phenomenon such as a pressure, typically at around room temperature.

As used herein, the term "non-flowable", or any grammatical deflection thereof, in the context of paste or dough-like compositions relates to a non-fluid consistency at around the room temperature.

The term "non-flowable" also encompasses a viscous solution. The term "viscous solution" refers to a solution that has an increased resistance to flow, yet is capable of deformed and reform, typically, but not exclusively, having a static high viscosity. In some embodiments, the paste has a high viscosity at rest and room temperature. In some embodiments, the paste provides a substantially homogeneous dispersion of the crosslinked polysaccharide.

As used herein, the term "high viscosity" means that the paste cannot be easily squeezed out when being applied. In some embodiments, the paste is also characterized by high viscosity (e.g., above 35 Pa·s) at stationary state, but can still adhere firmly to a tissue, such as bone tissue.

The composition may have a viscosity and potency which is high enough to permit its hemostatic effective use by a surgeon e.g., to allow placing the paste over the bleeding site.

The terms "liquid medium", "medium", "dispersing agent" or "dispersant" may be used hereinthroughout interchangeably. Herein, the term "dispersant" is meant to refer to a liquid medium, optionally a liquid medium having a viscosity having, or is capable of providing a pasty and/or dough-like consistency.

The term "at rest" is used herein to not being agitated or flowing, e.g., being at a stationary state.

As used herein, the term "around room temperature" should be understood to mean at least one temperature ranging from about 20° C. to about 30° C., e.g., 20 to 25° C.

The term "homogeneous dispersion" refers to a uniform mixture, that is, no separation of two or more phases in the mixture is discernible to the naked eye.

As used herein, the term "substantially homogeneous dispersion" means that at least 90%, optionally at least 99%, and optionally at least 99.9% of the total amount of the dispersion is a uniform mixture.

The term "degradable" may refer to hydrolytic degradation as a result of, inter alia, a chemical or thermal reaction, an enzymatic degradation, or a reaction induced by radiation. For example, the composition may be degraded in physiological conditions within a short period of time because of the amylase in the plasma. Embodiments of degradation rate are provided hereinbelow.

Physiological conditions may encompass aqueous-based milieu having a temperature in a range of about 20 to about 40° C. and a pH of about 6 to about 8, an atmospheric pressure of about 0.8 atm to about 1.2 atm, or corresponding atmospheric oxygen concentrations.

The term "hemostatic" refers to an ability to prevent, reduce, or stop blood loss e.g., from wounds, such as surgical or traumatic wounds, e.g., by promoting blood clot formation.

The term "powder" refers to solid particulate material, typically, to dispersed dry solid particles, e.g., in the form of a plurality of particles of a solid characterized by small size, typically, within the range of from 0.1 to 1000 micrometers, at times below 100 micrometer.

The term "solid" characterizes the state of the compound or composition at room temperature (e.g., 25° C.) and at atmospheric pressure (760 mmHg), i.e. a compound or a composition of high consistency which retains its form during storage. This term in the present application also relates to non-fluid particles, or dissolved substance. As opposed to "liquid" compounds and compositions, the solid does not flow under its own weight.

"Powdered" and "particulate" may be used interchangeably herein.

The term "paste" as used herein, relates to the consistency of the composition at at-least one temperature around the room temperature, and defines a fluid mixture of solid particles. Typically, paste has no fixed shape, and is therefore not a solid or a gas. The term "paste" according to the present disclosure may also include slurry, salve, and ointment. Slurry may functionally be regarded as a thin, oily paste. A paste according to the present disclosure may also include pores comprising of an expandable gas, such as air. Accordingly, in some embodiments, the composition is a paste, or is in pasty consistency at at-least one temperature in the range of 10° C. to 37° C.

In some embodiments, the composition is in the form of non-flowable paste. The term "non-flowable" (or "not flowable") paste is also referred to herein as "putty". The terms "putty", or "dough-like" refer to a doughier consistency at 37° C. which takes longer to settle, and has a better shape retention than a "flowable" paste. These terms indicate that the material cannot be stirred but only kneaded.

In some embodiments, the composition is bioabsorbable. The term "bioabsorbable" refers to the ability of a tissue-compatible material to degrade in the body after implantation into nontoxic products which are eliminated from the body or metabolized.

The embodiments of the present invention further relate to fast swelling, absorbable, biodegradable hemostatic non-flowable paste. In some embodiments, the composition (e.g., in the form of hemostatic paste) comprises at least three components. The first component comprises a xerogel powder. The second and the third components comprise dispersants. The powder may comprise cross-linked polysaccharide as described herein. In some embodiments, the cross-linked polysaccharide is synthesized by crosslinking using polyfunctional carboxylic acids such as citric acid (alternatively, without limitation, malic, tartaric, citric, malonic, succinic, glutaric, or adipic acid). A xerogel is obtained when the liquid phase of a gel is removed e.g., by evaporation. It typically exhibits shrinkage of greater than (>) 90%, by volume.

As used herein the term "polysaccharide" refers to a polymeric carbohydrate having a plurality of repeating units comprised of simple sugars. The term "polymeric" or "polymer" is meant to include both oligomeric and polymeric units and, typically, those polysaccharides having more than four repeating monomeric simple sugar units.

The xerogel, such as cross-linked-CMS, or hyaluronic acid, can form hydrogel when placed in contact with aqueous environments, such as body fluids.

A hydrogel is a network of polymer chains that are typically hydrophilic, sometimes found as a colloidal gel in which water is the dispersion medium.

In some embodiments, the polysaccharide comprises milled polysaccharide. The term "milled" relates to being grinded e.g., into powder form, by any method known in the art.

The term "substantially anhydrous blend" is intended to mean that the content of water in the blend does not exceed about 5% or about 3%, by weight.

In some embodiments, the crosslinked polysaccharide comprises polysaccharide e.g., CMS, or HA, that is cross-linked by reaction via a polyfunctional carboxylic acid. In some embodiments, the acid may be selected malic acid, tartaric acid, citric acid, malonic acid, succinic acid, glutaric acid, or adipic acid, or any mixture thereof. In exemplary embodiments, the acid comprises citric acid.

In some embodiments, the cross-linked polysaccharide is suspended or dispersed within a substantially anhydrous blend of a glycerol and at least one additional dispersant, such as PEG.

In some embodiments, cross-linked polysaccharide, CMS, or HA is in the form of a powder having average or median particle size less than 100 microns.

In some embodiments, the composition is substantially free of water or is substantially anhydrous. In some embodiments, the composition further comprises a neutralizing alkaline agent. In some embodiments, the paste comprises less than 5%, or less than 1%, of water.

In some embodiments, the glycerol is present at a weight concentration of 15 to 30%, e.g., 15%, 16%, 17%, 18%, 19%, 20%, 21%, 22%, 23%, 24%, 25%, 26% 27%, 28%, 29%, 30%, 31%, 32%, 33%, 34%, or 35%, including any value and range therebetween.

In some embodiments, the PEG is present at a weight concentration of 10 to 25%, e.g., 10%, 11%, 12%, 13%, 14%, 15%, 16%, 17%, 18%, 19%, 20%, 21%, 22%, 23%, 24%, or 25%, including any value and range therebetween.

In some embodiments, the glycerol is present at a weight concentration of 15 to 30%, and the PEG is present at a weight concentration of 10 to 25%.

In some embodiments, the polysaccharides micro particles are dispersed in dispersants such that the dispersants maintain the anhydrous environment and makes the hemostatic composition hygroscopic. Once contact with moisture (blood), the dry particles absorb water very fast and swell allowing to fill the micro-structure or cavities of e.g., bone tissue to achieve hemostasis.

In some embodiments, the polysaccharide substantially does not absorb the dispersants which are anhydrous but hydrophilic, e.g., glycerol and PEG. Despite glycerol and PEG are hydrophilic, in some embodiments, the particles are still capable to rapidly absorbing blood, plasma, water, or bodily fluids.

Without wishing to be bound by any theory, the non-aqueous dispersants are outside of the crosslinked network particles and should not influence their ability to absorb liquids. The absorption would appear to be maximized by eliminating pre-swelling or pre-load.

In some embodiments, the particles do not swell or absorb the selected dispersants but can quickly swell when provided with plasma and absorb the greatest % of plasma components.

In some embodiments, the selected dispersants should not shield the crosslinked network particles from the plasma components that are intended to be absorbed.

In some embodiments, the xerogel crosslinked powdered polysaccharide has a swelling capacity in water of at least 10 times, e.g., 10 times 15 times, 20 times, or 25 times, including any value therebetween of its dry weight at 25° C., optionally within less than 2 min, e.g., about 1 min.

In some embodiments, the xerogel crosslinked powdered polysaccharide has a swelling capacity in water of at least 10 times, e.g., 10 times 15 times, 20 times, 25 times, or 30 times, including any value therebetween of its dry weight at 25° C. optionally within less than 2 min, e.g., about 10 to 20 min.

Without being bound by any particular theory or mechanism, upon placing in aqueous environment, powerful osmotic action dehydrates allows the xerogel to swell to at least 10 times of the dry xerogel volume to fill up a wound and produce a "back pressure" in a confined wound space to simulate tamponade effect and enhance the natural clotting process. The deformability of the inventive composition also ensures its accessibility to narrow spaces and its application to uneven surfaces, making it a useful material to address the intra-operational bleeding or oozing. The instant composition is particularly suitable for hard to access wounds such as cavity bleeding, e.g., in bone tissues.

In some embodiments, the xerogel crosslinked powdered polysaccharide features a degradation rate of 75% to 95%, by initial weight, in physiological conditions (e.g., in vivo) in 3 d. In some embodiments, the xerogel crosslinked powdered polysaccharide features a degradation rate of 75%, 80%, 85%, 90%, or 95%, by initial weight, including any value and range therebetween, in physiological conditions (e.g., in vivo) in 3 d.

In some embodiments, the xerogel crosslinked powdered polysaccharide features a degradation rate of 55% to 85%, by initial weight, in physiological conditions (e.g., in vivo) in 1 d. In some embodiments, the xerogel crosslinked powdered polysaccharide features a degradation rate of 55%, 60%, 65%, 70%, 75%, or 80%, by initial weight, including any value and range therebetween, in physiological conditions (e.g., in vivo) in 1 d.

In some embodiments, the xerogel crosslinked powdered polysaccharide features a degradation rate of 50% to 80%, by initial weight, in physiological conditions (e.g., in vivo) in 3 h. In some embodiments, the xerogel crosslinked powdered polysaccharide features a degradation rate of 50%, 55%, 60%, 65%, 70%, 75%, or 80%, by initial weight, including any value and range therebetween, in physiological conditions (e.g., in vivo) in 3 h.

In some embodiments, the xerogel crosslinked powdered polysaccharide features a degradation rate of 0.1% to 25%, by initial weight, in physiological conditions (e.g., in vivo) in 30 min. In some embodiments, the xerogel crosslinked powdered polysaccharide features a degradation rate of 0.1%, 1%, 5%, 10%, 15%, 20%, or 25%, by initial weight, including any value and range therebetween, in physiological conditions (e.g., in vivo) in 30 min.

In some embodiments, the xerogel crosslinked powdered polysaccharide features a degradation rate of 0.1% to 25%, by initial weight, in physiological conditions (e.g., in vivo) in 30 min, and degradation rate of 55% to 85%, by initial weight, in physiological conditions (e.g., in vivo) in 1 d.

Figure 3:
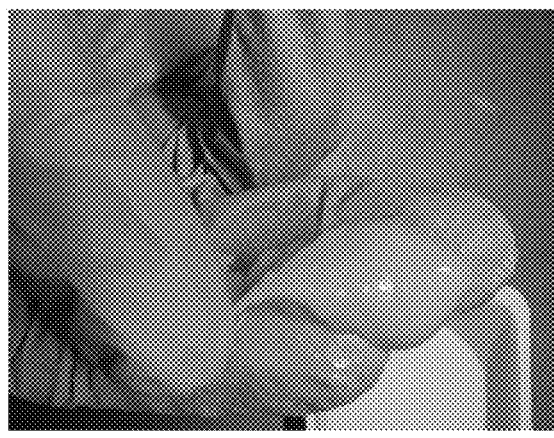
FIG. 3 presents a photographic image showing that CMS formulation which contains both propylene glycol and PEG400 (1:1 ratio by weight), the hemostat is still sticky to nitrile gloves.
Figure 4A:
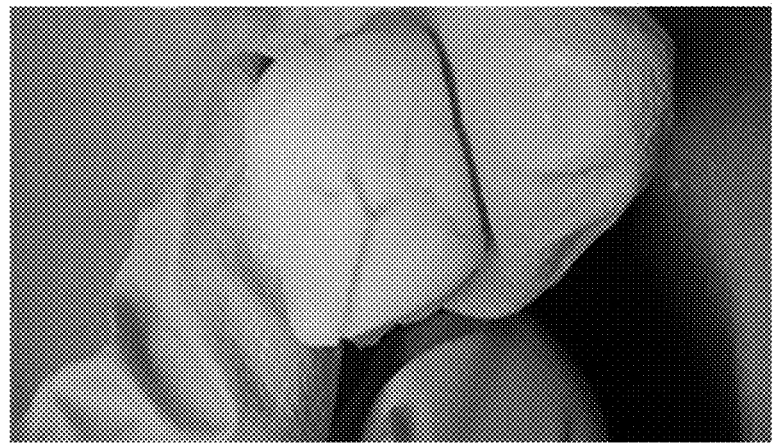
FIG. 4A-D present photographic images of CMS pastes with four different PEG to glycerol ratios, 1:1.3, 1:1.7, 1:2.2, and 1:2.7, respectively: when the ratio is 1:1.3 (FIG. 4A), the sample was dry and easy to crack during kneading by hand; when the ratios are 1:1.7 (FIG. 4B) and 1:2.2 (FIG. 4C), the samples were easy to deform by kneading: it is therefore suggested that these ratios are the appropriate PEG to glycerol range; when the ratio is increased to 1:2.7, the sample was too thin, somehow flowable, and was very sticky to gloves (FIG. 4D)
Figure 4B:
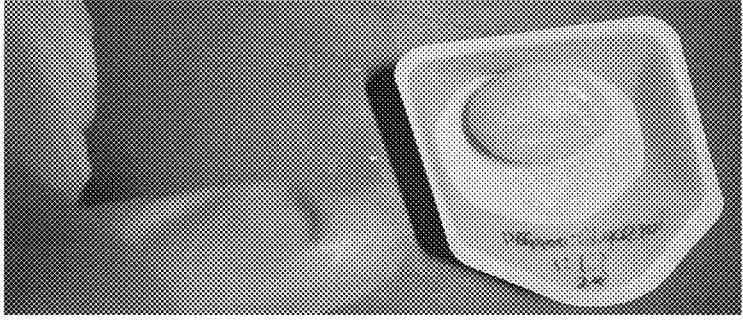
Figure 4C:
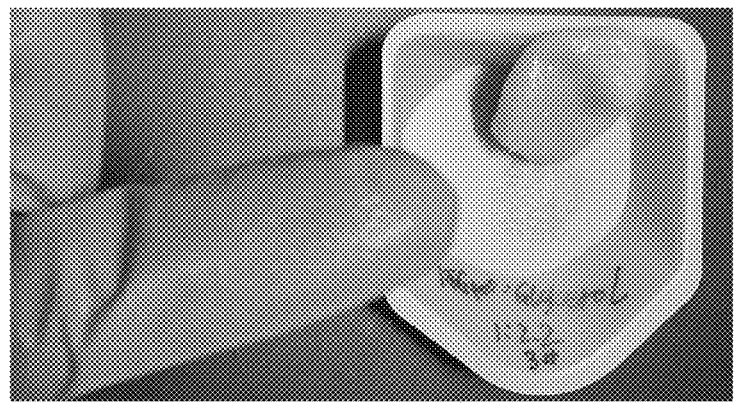
Figure 4D:

In some embodiments, the composition is substantially devoid of polyethylene glycol. By "substantially devoid of polyethylene glycol", it is meant that the polyethylene glycol may be present at low concentration. e.g., 10%, 9%, 8%, 7%, 6%, 5%, 4%, 3%, 2%, 1%, or less, by total weight of the dispersants, or is completely absent. In this respect, reference is made to FIG. 3 presenting a photographic image showing that PEG-to-propylene glycol 1:1, the paste sticks to the gloves.

In some embodiments, the composition is characterized by adhesiveness (also referred to as "bond strength") of 2.5 to 4 N/m, as tested using a T-peel test. In some embodiments, the composition is characterized by adhesiveness of 3.5 to 4 N/m, as tested using a T-peel test. In some embodiments, the composition is characterized by adhesiveness of 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, or 4.5 N/m, including any value and range therebetween, as tested using a T-peel test.

The unit "N/m" (i.e. average load/width) as used herein refers to peel strength when the tested body and the sealing sheet are bonded together, with a bonding portion between the tested body and the sealing sheet being cut to a width of a certain mm and a T peel test being made on this cut piece as a test sample. This test is referred to as a "T-peel" test because as the two adherends are pulled apart, they form the shape of a "T".

The T-peel test as used herein is a test based on a measurement according to the ASTM F2256-05(2015) entitled: "Standard Test Method for Strength Properties of Tissue Adhesives in T-Peel by Tension Loading", with the modification of using silicon sheet instead of porcine skin.

In some embodiments, the composition is characterized as being non sticky to gloves. In some embodiments, the composition is characterized as being non sticky to nitrile, e.g., nitrile gloves.

The term "non-sticky" as used herein, refers to a composition that is sufficiently smooth and/or sufficiently solid so that no detectable portion of the product will remain adhered on the undesired surface (such as that of a nitrile glove) when the composition is removed therefrom, and at times "non-sticky" refers to a composition that a practitioner can also readily hold with their glove covered hand without any significant or visible residue being left behind on the glove upon removing the composition therefrom.

In some embodiments of the composition, the xerogel is characterized by crosslinking degree (also referred to as "crosslinking density"; (p)) of 0.0040 to 0.0060, or 0.0047 ("0.4x") to 0.0054 ("4x") mole/mL (mole of crosslinks per unit volume according to the equations (1) to (4) described in the Examples section below; reference is made to Omidian et al., Iranian J. of Polymer Science and Technology Vol 3 No 2, 1994). In some embodiments of the composition, the xerogel is characterized by crosslinking density of 0.0040, 0.0041, 0.0042, 0.0043, 0.0044, 0.0045, 0.0046, 0.0048, 0.0049, 0.0050, 0.0051, 0.0052, 0.0053, 0.0054, 0.0055, 0.0056, 0.0057, 0.0058, 0.0059, or 0.0060 mole/mL, including any value and range therebetween. In exemplary embodiments, embodiments, the crosslinking density is about 0.0047 mole/mL.

Figure 1:
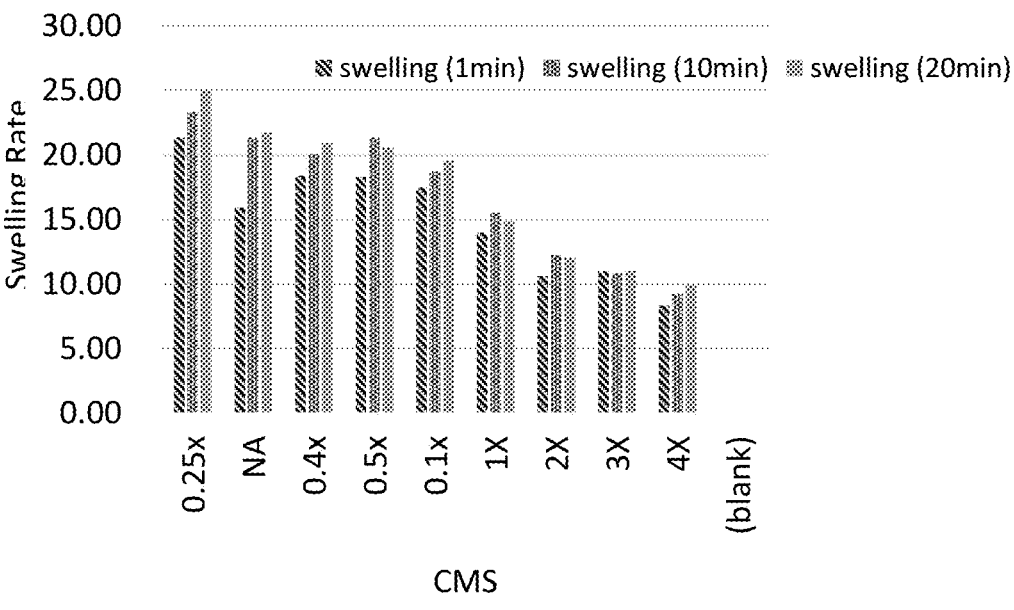
FIG. 1 presents a bar graph demonstrating the swelling property of the carboxymethyl starch (CMS)-citric acid (CA) xerogel made from different amounts of CMS and CA crosslinking agent (see Table 1A); in each triplet, from left to right: swelling rate after 1 min; swelling rate after 10 min, and swelling rate after 20 min (data are presented in Table 4; swelling rate refers to increased times of the xerogel i.e. by how many times has the xerogel increased compared to xerogel prior to immersion in liquid, by weight)

Reference is made to FIG. 1 showing that swelling rate of xerogels made by crosslinking CMS with a relatively high dose of citric acid (1x or higher) are inversely proportional to the concentration of the citric acid, and with the 0.25x to 1x cross linking ratio, the swelling proportion is at least 15 times of the xerogel. However, as shown in FIG. 5, in terms of the degradation degree at the beginning, only for the cross-linked samples, the degradation rate was reversely proportional to the crosslinking rate, and at longer time points the degradation rates were similar in all sample groups, indicating that the overall degradation profile of the CMS-CA is affected by the crosslinking rate. Therefore, taken together, in some embodiments crosslinking rate of 0.25x to 1x may be desired.

In some embodiments, the term "crosslinked" and/or "crosslinking", as used herein, and any grammatical derivative thereof refers generally to a chemical process or the corresponding product thereof in which two chains of polymeric (e.g., anhydroglucose) units are attached by bridges, covalent or non-covalent. A "cross-linker", composed of an element, a group or a compound may join certain carbon atoms of the chains by primary chemical. Non-limiting exemplary cross-linkers are described herein.

In some embodiments, the composition is sterile. The term "sterile" as used herein means having a low bioburden, effectively being germ-free, e.g., being free from microorganisms, e.g., bacteria and viruses. Sterilization is the process of reducing the bioburden to an effectively germ-free level.

In some embodiments, the paste is supported on a substrate that is a flexible bioabsorbable sheet.

According to another aspect of present invention, there is provided a method for treating blood loss injuries applying the disclosed composition in an embodiment thereof in/on the injured site, e.g., being a bone tissue.

According to another aspect of present invention, there is provided a method of making a non-flowable composition (e.g., in the form of hemostatic paste) comprising the steps of: providing cross-linked polysaccharide in the form of a powder having average or median particle size of less than 100 microns; adding glycerol into the polysaccharide powder, and mixing the glycerol with the powder until a homogeneous non-flowable and/or dough-like material is formed; adding PEG to the non-flowable/dough-like material and mixing the PEG with the non-flowable/dough-like material thoroughly; thus forming the non-flowable composition (e.g., in the form of hemostatic paste). Non-limiting exemplary polysaccharides (e.g., CMS and HA, such as in the form of xerogel) are described hereinabove.

According to another aspect of present invention, there is provided a method of making a non-flowable composition (e.g., in the form of hemostatic paste) comprising the steps of; cross-linking polysaccharide by mixing polysaccharide a cross-linker in an embodiment thereof, such as citric acid, in presence of water and reacting the polysaccharide with citric acid at elevated temperature, e.g., above 40° C., such as about 65° C.; substantially drying the cross-linked polysaccharide; milling the cross-linked polysaccharide to a powder having average or median particle size of less than 100 microns; adding glycerol into the polysaccharide powder, and mixing the glycerol with the powder until a homogeneous dough-like material is formed; adding PEG to the dough-like material and mixing the PEG with the dough-like material thoroughly; thus forming the non-flowable composition (e.g., in the form of hemostatic paste).

The cross linking may be carried out by combining a cross-linker e.g., citric acid to the polysaccharide (e.g., CMS) at a weight ratio of cross-linker to polysaccharide of 1:7 to 1:75, or 1:60 to 1:72, by weight.

In some embodiments, the drying is carried out by heating the polysaccharide and acid mixture to more than 60° C., or more than 100° C., e.g., about 140° C. In some embodiments, the heating is carried out for 25 min e.g., in a preheated incubator. In some embodiments, the heating allows to accomplish the crosslinking. Typically, prior to the drying step, the mixture is dough-like, and after heating, the mixture turns into a hard material and can be grinded by grinding equipment.

In some embodiments, the method further comprises a step of dissolving a neutralizing alkaline agent which, in some embodiments, may be present in the glycerol-containing dispersant, at a temperature above 65° C. prior to addition to the polysaccharide xerogel.

According to another aspect, there is provided a method of making a wound dressing containing the composition (e.g., in the form of hemostatic paste) according to an embodiment thereof, the method comprising a step of applying the disclosed composition (e.g., hemostatic paste) onto at least one face of a flexible bioabsorbable sheet substrate.

According to some embodiments of the present invention, there is provided a method of using the composition (e.g., in the form of hemostatic paste) in an embodiment thereof, comprising the step of: applying the composition onto or into a bleeding tissue such as bone tissue or wound.

The term "tissue" refers to an association of cells and/or cell components united in carrying out a particular function. The cells in the tissue may be all of one type or of more than one type. The tissue can be an artificial tissue in which cells are grown to function in a similar manner as a tissue in a living organism. The tissue may be a human body tissue or an animal tissue, a soft tissue or a bone tissue. The method may be e.g., for performing tissue repair, and/or for providing tissue and organ supplementation, of treating a tissue defect, wound, and/or supplementing and replacing tissue remedying of a tissue defect, healing of a wound, or in need of a tissue supplement.

According to some embodiments of the present invention, there is provided a use of the composition (e.g., in the form of hemostatic paste) in an embodiment thereof in a method for treating a wound or bleeding tissue comprising applying the composition (e.g., in the form of hemostatic paste) in an embodiment thereof to a wound or bleeding tissue, such as bone tissue.

In another aspect, the present invention further provides a hemostatic kit comprising a container containing the herein disclosed composition in an embodiment thereof, e.g., xerogel crosslinked powdered polysaccharide dispersed within a substantially anhydrous blend of: dispersants selected from glycerol, and PEG, wherein the PEG and glycerol are present in a ratio between higher than 1.3:1 to below 2.7:1, by weight, respectively, and wherein the powder content in the composition is above 60% by weight. In some embodiments of the kit, the composition is in the form of a paste at around room temperature.

Any aspect and embodiment of the hereinthroughout disclosed composition may be incorporated to the aspect and embodiments of the kit, including embodiments of the composition, the dispersant, and/or the xerogel.

Alternatively, present invention provides a hemostatic kit comprising a container containing the herein disclosed xerolgel in an embodiment thereof, and another container comprising at least one of the dispersants (e.g., PEG or glycerol). In such embodiments, the kit may further contain a measuring means, e.g., a measuring cylinder, to measure the volume of the dispersant(s).

The hemostatic kit of the invention may be a kit for use in reducing, preventing or stopping blood flow, e.g., in open wounds, and it may be used for reducing, preventing or stopping blood flow during a procedure, such as during, before, or after a surgical procedure such as, for example, laparoscopic surgery, neurosurgery, abdominal surgery; orthopedic surgery such as knee surgery, head and neck surgery, surgery, joint and spinal surgery. The kit may be used for reducing or preventing blood flow from the tissue.

In one embodiment, this kit may be stored at room temperature, such as in a temperature in the range of 8 to 40° C., or at lower temperatures.

In some embodiments of any aspect of the kit or the composition disclosed herein, the blend may comprise an additive e.g., calcium salt and/or one or more excipients, e.g., selected from, without being limited thereto, one or more amino acids, albumin, saccharides, and/or saccharide derivatives.

The term "additive" is meant to be understood as any substance that can be added to a composition, and may also include an active additive such as calcium salt as described below.

The term "excipient" as used herein denotes a non-active or non-therapeutic agent added to a pharmaceutical composition e.g., to provide a desired consistency or stabilizing effect.

In another aspect of the present invention, there is provided a method of treating a wound and/or bone tissue comprising the step of applying (e.g., contacting) the composition in any aspect and embodiment thereof onto and/or into the wound of a subject in a need thereof.

By "treating a wound" it further meant to encompass reducing blood loss at a bleeding site of a tissue, e.g., in a patient undergoing surgery.

Accordingly, in some embodiments, the method is for reducing blood loss at a bleeding site of a tissue. e.g., in a subject undergoing surgery, comprising contacting the disclosed composition or formulation in an embodiment thereof with the bleeding site.

As used herein, the term "subject" shall mean any animal including, without limitation, a human, a mouse, a rat, a rabbit, a non-human primate, or any other mammal. In some embodiments, the subject is human, e.g., a human patient. The subject may be male or female.

It is intended that at least the embodiments relating to a xerogel crosslinked powdered polysaccharide, the anhydrous blend of glycerol, and PEG, their respective ratio, and the powder content in the composition by weight, be included in all aspects disclosed in the present application.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

The term "about" as used herein means that values that are ±10% the indicated value are also intended to be included. Generally, all values in this application are intended to include the term "about".

The terms "comprises", "comprising", "includes", "including", "has", "having", "contain", "containing", and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" in the context of medical treatment includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "bleeding" refers to extravasation of blood from any component of the circulatory system. A "bleeding" thus encompasses unwanted, uncontrolled and often excessive bleeding in connection with surgery, trauma, into the tissue defect or other forms of tissue damage, as well as unwanted bleedings in patients having bleeding disorders.

The term "trauma" is defined as an injury caused by a physical force; non-limiting examples include the consequences of vehicle accidents, gunshots and burns.

As used herein, the terms "controlling", "preventing", or "reducing", which may be used herein interchangeably in the context of the bleeding, including any grammatical inflection thereof, indicate that the rate of the blood extravagated is essentially nullified or is reduced by 10%, at least 20%, at least 30%, at least 40%, at least 50%, at least 60%, at least 70%, at least 80%, at least 90%, or even by 100%, of the initial rate of bleeding, compared to situation lacking the contact of the disclosed composition in/on the bleeding site. Methods for determining a level of appearance of bleeding are known in the art. Further, in some embodiments, the terms "controlling", "preventing" or "reducing", in the context of the bleeding are also meant to encompass at least partially sealing blood vessels at the bleeding site e.g., in soft tissues.

In those instances where a convention analogous to "at least one of A. B, and C, etc." is used, in general such a construction is intended in the sense one having skill in the art would understand the convention (e.g., "a composition having at least one of A, B, and C" would include but not be limited to compositions that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Example 1 Making the Hemostatic Paste and Paste Composition

Carboxymethyl starch (CMS) was cross-linked by citric acid as follows. The sodium salt of the CMS was used for the synthesis of the hydrogels. The cross-linking agent (citric acid from the Guangzhou chemical reagent factory) was first dissolved in distilled water and then was thoroughly homogenized with the CMS (purchased from Shanghai Aladdin Biochemical Technology Co., Ltd; the respective amounts are described below) resulting in a homogeneous dough-like product. The dough-like product was then chopped into small chunks. The product was heated at 140° C. for 25 min in a preheated oven to accomplish cross-linking. The obtained product—cross-linked CMS (CMS-CA) which can be referred to as a xerogel or dried compact hydrogel was dried at 70° C. overnight and then ground to an average particle size of below 100 μm.

Cross-linking degree Calculations: the cross-linking ratio during the synthesis process may be referred to as "no. x", see Table 1A below.

Calculating the crosslinking degree is performed using equations below (see Omidian et al., Iranian J. of Polymer Science and Technology Vol 3 No 2, 1994):

$$\rho = \rho_1 + (1 - \rho_1/\rho_2) \times C \quad (1),$$

where $\rho$ is the density of the hydrated sample, $\rho_1$ is the density of the saline (1.03 g/mL), $\rho_2$ is the density of the dry xerogel and C is the hydrogel concentration in saline (g/mL);

$$V_m = M/\rho_2 \quad (2),$$

where $V_m$ is the molar volume of the CMS monomer, and M is the molecular weight of the CMS monomer.

The CMS chain molecular weight Me can be roughly calculated as:

$M_c$ should be the Mw of the crosslinker (citric acid; CA);

The amount (mol/mL) of reacted crosslinker, or crosslinking degree is $$(v/V) = \rho/M_c \quad (3).$$

Table 1A presents amount of the citric acid that were used for different "x". Thus, the measured the swelling volume of a crosslinked CMS sample of 0.4×, 2× and 4× is used to calculate the crosslinking degree (Table 1B): in exemplary procedures, the xerogel powder was placed in the graduated cylinder for a rough estimate of the V of xerogel. To measure the V final, saline (Sodium Chloride was purchased from Guangzhou chemical reagent factory) was added to the xerogel followed by waiting for its complete swelling, then using the cylinder to measure the V final.

TABLE 1A

| Amount of the citric acid used for different "x" | | |
|---|---|---|
| Sample | CMS (g ) | CA (g) |
| CMS-CA (0.4 x) | 70 | 1.04 |
| CMS-CA (0.5 x) | 70 | 1.30 |
| CMS-CA (2.0 x) | 50 | 3.74 |
| CMS-CA (3.0 x) | 50 | 5.60 |
| CMS-CA (4.0 x) | 50 | 7.47 |

TABLE 1B

| Origina volume and final volume (92 h) of crosslinked CMS samples in saline. | | | |
|---|---|---|---|
| | CMS 0.4 x | CMS 2 x | CMS 4 x |
| M sample (g) | 1 | 1 | 1 |
| V xerogel (cm³) | 1.4 | 1.2. | 1.0 |
| V final (mL) | 8.5 | 5.1 | 3.9 |

Based on the equations (1). (2), (3) and (4), the crosslinking degree p crosslinker of different crosslinked CMS samples is shown in Table 2.

TABLE 2

| Crosslinking degree for 0.4 x, 2 x and 4 x of crosslinked CMS samples. | | | |
|---|---|---|---|
| | CMS 0.4 x | CMS 2 x | CMS 4 x |
| $\rho_1$ (g/mL) | 1.03 | 1.03 | 1.03 |
| $\rho_2$ (g/mL) = M sample/Vxerogel | 0.71 | 0.83 | 1.00 |
| $C_2$ (g/mL) = M sample/V final | 0.12 | 0.2 | 0.26 |
| M (=$M_w$ of CMS monomer)** | $7.5 \times 10^5$ | $7.5 \times 10^5$ | $7.5 \times 10^5$ |
| $\rho$ (g/mL) | 0.91* | 0.98 | 1.03 |
| $V_m$ (=M/$\rho$2) (ml/mol) | $10.6 \times 10^5$ | $9.0 \times 10^5$ | $7.5 \times 10^5$ |
| $M_c$ (gr/mol)** | 192.13 | 192.13 | 192.13 |
| $\rho$ crosslinker (mol/mL) (=p/$M_c$) | 0.0047 | 0.0051 | 0.0054 |

*Calculation example: 1.03 + (1 − 1.03/0.71) × 0.26; molecular weight of the monomer should be the MW of the CMS, which is 7.5 × 10⁻5, and the network chain $M_w$, $M_c$ is the $M_w$ ofthe citric acid.

Dispersing the resulting cross-linked CMS powder: next, cross-linked CMS powder was mixed with dispersants as follows. Glycerol was added into powder, and mixed/stirred until al powder particles are coated by glycerol, forming a dough-like paste. Then propylene glycol or PEG 400 was added to the above paste, and mixed/stirred, to form the final, non-flowable hemostatic paste. The amount of each component added is shown in Table 3.

TABLE 3

| | | CMS-CA | PG | Glycerol | PEG400 | % CMS- | PG/ | PEG400/ |
|---|---|---|---|---|---|---|---|---|
| Sample name | Polymer | (g) | (g) | (g) | (g) | CA** | glycerol | glycerol |
| G80606_1 | CMS-CA | 6 | 1.4795 | 2.52 | 0 | 60 | 1:1.7 | NA |
| G80606_2 | CMS-CA | 6 | 1.25 | 2.75 | 0 | 60 | 1:2.2 | NA |
| G80606_3 | CMS-CA | 6 | 1.08 | 2.92 | 0 | 60 | 1:2.7 | NA |
| G80606_4 | CMS-CA | 6 | 0 | 2.75 | 1.25 | 60 | NA | 1:2.2 |

Content table of CMS-CA samples (particle size is <100 for all samples; cross-linking ratio: 0.4 x*))

TABLE 3-continued

| | | Content table of CMS-CA samples (particle size is <100 for all samples; cross-linking ratio: 0.4 x*)) | | | | | | |
|---|---|---|---|---|---|---|---|---|
| Sample name | Polymer | CMS-CA (g) | PG (g) | Glycerol (g) | PEG400 (g) | % CMS-CA** | PG/ glycerol | PEG400/ glycerol |
| G80606_5 | CMS-CA | 6 | 0 | 2.92 | 1.08 | 60 | NA | 1:2.7 |
| G70801_1 | CMS-CA | 6 | 0 | 3 | 2.32 | 60 | NA | 1:1.3 |

*It was found that 0.4 x ratio in this bone hemostat is appropriate, see below.
**60% of CMS can make the hemostat non flowable and be easy to be manipulated with hands. Thus, the percentage of CMS should neither be too low, nor too high, in order to maintain its current appearance, which was found suitable for bone hemostasis.

Example 2 Swelling Properties of Cross-Linked CMS and Other Polysaccharides

For swelling testing, one gram of xerogel was immersed in excess saline at room temperature for certain period to reach swelling equilibrium. At time intervals of 1, 10, 20 min, swollen samples were separated from the unabsorbed saline by filtering through a 100-mesh screen. Swelling percent at each time point was calculated using the following formula Equation:

$$SP=100(M_t-M_d)/M_d,$$

where SP is the swelling percent, $M_t$ and $M_d$ are the weights of swollen hydrogel particles at time t and dry xerogel particles, respectively.

Referring to FIG. 1 and Table 4, the swelling of CMS-CA xerogels is shown in saline at 1 min, 10 min and 20 min after immersion, with significant swelling of the order of 1500% at 1 min and 2000% at 20 min observed experimentally.

Further Referring to FIG. 1 and Table 4, the swelling of CMS based xerogels crosslinked by different amount of citric acid is compared upon exposure to saline at 1 min, 10 min, and 20 min after immersion. The data show that the swelling rate of xerogels made by crosslinking CMS with a relatively high dose of citric acid (1× or higher) are inversely proportional to the concentration of the citric acid. Thus, by adding different amount of citric acid, the swelling rate of the hydrogel can be adjusted.

TABLE 4

| | Swelling rate data for samples with different crosslinking degrees | | |
|---|---|---|---|
| CMS-CA | Swelling (1 min)* | Swelling (10 min)* | Swelling (20 mm)* |
| 0.25x | 21.35 | 23.34 | 25.00 |
| NA** | 15.94 | 21.35 | 21.72 |
| 0.4x | 18.41 | 20.07 | 20.89 |
| 0.5x | 18.31 | 21.36 | 20.61 |
| 0.1x | 17.50 | 18.73 | 19.57 |
| 1x | 14.00 | 15.50 | 14.89 |
| 2x | 10.64 | 12.26 | 12.07 |
| 3x | 11.01 | 10.85 | 11.02 |
| 4x | 8.36 | 9.25 | 9.94 |

*The swelling values are presented in terms the increased times of the xerogel weight after absorbing saline in the indicated time: 1 min, 10 min and 20 min;
**non-cross-linked.

Example 3 Dispersant Comparison and their Impact on Adhesiveness

To make a paste form hemostat, two organic dispersants are used. The glycerol was used in every formulation. The glycerol is friendly used medical field and is safe.

while another dispersant was chosen between propylene glycol (PG) and polyethylene glycol (PEG) 400.

For all the samples, unless otherwise specified, are cross-linked 0.4×CMS at 60% by weight.

Referring to Table 5 below, the glycerol amount in 10 g of paste was 2.52-2.92 g. PG was used in three formulations (G180606_1, G180606_2 and G180606_3), and PEG400 is used in two formulations (G180606_4 and G180606_5). The adhesiveness of each formulation was then tested using T Peel test.

Exemplary procedures for T-peel test is based on ASTM F2256-05(2015) using a silicone sheet and includes:

a. Weighed 1 g sample (paste) was applied on the surface of silicon sheet followed by saline spraying;

b. Another silicon sheet was put above the paste with 5 min compression by heavy weights; segment was cut to strips of 15×2 cm to fit the silicone sheets.

c. Prepared sheets were transferred to Instron and the adhesion force was measured according to ASTM F2256-05(2015).

d. The force needed to separate the two adhered layers from one another (known as peel force) was measured using Instron 5944/100N sensor.

TABLE 5

| | Dispersants used in different formulations, and the respective adhesive force | | | |
|---|---|---|---|---|
| Sample | Adhesiveness N/m | PG (g/10 g paste) | Glycerol (g/10 g paste) | PEG400 (g/10 g paste) |
| G80606_1 | 5.33 | 1.48 | 2.52 | 0.00 |
| G80606_2 | 4.60 | 1.25 | 2.75 | 0.00 |
| G80606_3 | 5.66 | 1.08 | 2.92 | 0.00 |
| G80606_4 | 3.96 | 0.00 | 2.75 | 1.25 |
| G80606_5 | 3.99 | 0.00 | 2 92 | 1.08 |

Figure 2:
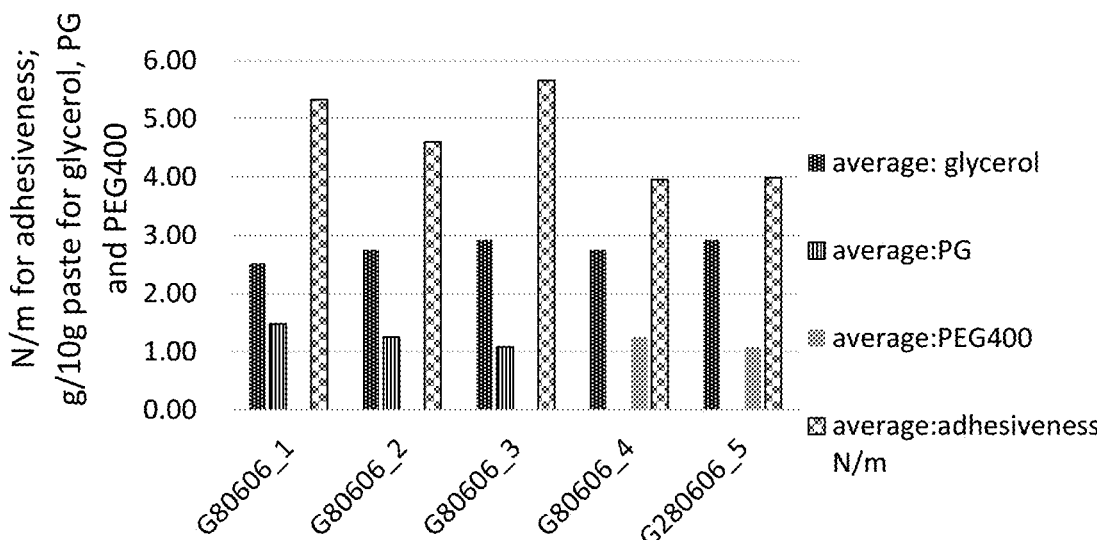
FIG. 2 presents a bar graph showing the adhesive force tested for different formulations samples (detailed in Tables 3 and 5): when propylene glycol (PG) is replaced with polyethylene glycol (PEG)400, the adhesive force decreases ($p<0.05$); each triplet refers to a tested sample with the Y-axis being: N/m for adhesiveness, and g/10 g paste for the dispersant tested, average of 3 tested samples for each.

A bar graph comparing the adhesive forces is shown in FIG. 2. The adhesive force of the PG group is stronger than that of the PEG400 group (p<0.05). Nevertheless, as described below, it was further found that when the formulation contains PEG400, it becomes less sticky to gloves.

PEG400 dosage determination: to address bone bleeding, one of the needs is the ease of use of the product. Normally, practitioners use the hemostat by hand, like bone wax. Thus, one of the requirements of the present concept is the composition not being sticky to gloves. The decrease in adhesive force when PG is replaced by PEG400 provides direct evidence that the PEG400 contribute directly to the ease of use of this bone hemostat. Accordingly, it was visually observed that when the formulation contained both propylene glycol and PEG400 (1:1 by weight) the hemostat was sticky to gloves and when the prototype contained propylene glycol, it was stickier, and it adhered to gloves (nitrile gloves were used in exemplary procedures). In this respect, propylene glycol is less preferred. Reference is made in this respect to FIG. 3 presenting a photographic image showing that PEG-to-propylene glycol 1:1, the paste sticks to the gloves.

When the propylene glycol was fully replaced by PEG400, although the adhesiveness decreased a little bit, it did not adhere to gloves any more. Additionally, the PEG400-containing prototype is as effective as the propylene glycol one in hemostasis as shown below.

As the result, PEG400 was used instead of propylene glycol for bone hemostat.

In additional exemplary procedures, four different PEG400 to glycerol weight ratios, 1:1.3, 1:1.7, 1:2.2, and 1:2.7, respectively, were tested (see FIGS. 4A-D). When the ratio was about 1:1.3, the sample was dry and easy to crack during kneading by hand. When the ratios are 1:1.7 and 1:2.2, the samples were easy to deform by kneading. It is suggested that these ratios are the appropriate PEG to glycerol range. When the ratio increased to about 1:2.7, the sample was too thin, somehow flowable, and was very sticky to nitrile gloves (also known as acrylonitrile butadiene rubber; Medicom). It is to note, again, that paste with PEG-to-propylene glycol 1:1, by weight, also resulted in the paste being stick to the gloves.

Referring to Table 6, when the ratio is 1:1.3, the sample was too thin, which means it could not stay at the bleeding surface. Also, the sample became less and less flowable when the PEG400 dosage was reduced.

TABLE 6

| Samples with different PEG/glycerol weight ratio (the cross-linking ratio is 0.4x) | | | | |
|---|---|---|---|---|
| PEG400/glycerol | CMS-CA (g) | Glycerol (g) | PEG400 (g) | Adhesiveness |
| 1:1.3 | 6 | 2.26 | 1.74 | NA (too thin) |
| 1:2.2 | 6 | 2.75 | 1.25 | 3.96 N/m |
| 1:2.7 | 6 | 2.92 | 1.08 | 3.99 N/m |

It is noteworthy that, as described below, both T-peel test and in-vivo test shown good results when the ratio was up to 1:2.7.

Example 4 Degradation Rate Vs. Crosslinking Agent Concentration

Normally, a starch-based material can be degraded by the body within a very short period of time because of the amylase in the plasma. For a hemostat, to maintain its function, the degradation profile should be slow at the very beginning and be fast once the hemostasis is achieved. To achieve this goal, adjusting the crosslinking rate was dictated by using different amounts of citric acid. It was found that the more citric acid was added, the more condense the xerogel particles were.

In exemplary procedures, the degradation rate was determined using phenol-sulfuric acid method: carbohydrates (simple sugars, oligosaccharides, polysaccharides, and their derivatives) react in the presence of strong acid and heat to generate furan derivatives that condense with phenol to form stable yellow-gold compounds that can be measured spectrophotometrically.

Thus, in exemplary procedures, glucose standard solution was first prepared, by adding 20.12 g of glucose to 500 mL of double distilled (dd) water. Next, each of 0.4, 0.6, 0.8, 1.0, 1.2, 1.4, 1.6 and 1.8 mL of the glucose solution respectively, were then taken and diluted to 20 mL with dd water. Chromogenic solution was then prepared by adding to the phenol solution (80%), 1.5 mL, to 18.5 mL of dd water to make the phenol solution of 6%. Next, 199.85 and 200.01 mg of the CMS, and 200.01 and 200.46 mg of CMS-CA (0.5, 1, and 4x) were weighted, and 5 mL of phosphate buffered saline (PBS) solution was poured to each sample.

For obtaining the standard curve, 5 mL of the chromogenic solution was added to each of the glucose solutions as described above. Next, 5 mL of the chromogenic solution was added to the samples containing the PBS. The standard curve solutions and the sample solutions were heated in boiling water for 30 min, and thereafter were cooled in ice.

The standard samples and the testing samples were added to 96-well plate (n=2), followed by measuring the absorbance value at 490 nm.

The results are summarized in Table 7 and FIG. 5. At the beginning, the degradation rate was reversely proportional to the crosslinking rate. At longer time points the degradation rates were similar in all sample groups, indicating that the overall degradation profile of the CMS-CA is affected by the crosslinking rate.

From the results it can be concluded that the condensed xerogel particles are more resistant to enzyme degradation at the beginning (just after the hemostat was applied). Once the enzyme in the plasma has adequate contact with the whole particle, the degradation is likely to accelerated according to the trend shown in Table 7 and FIG. 5. It is noteworthy that the bone hemostat needs a relatively rapid degradation rate, since it should not interrupt the bone tissue regeneration. Thus, 0.5x to 1x appear suitable for bone hemostasis.

TABLE 7

| Time serial data for CMS-CA degradation with different crosslinking rate | | | | |
|---|---|---|---|---|
| CMS-CA | % DE (0 d*) | % DE (3 H) | % DE (1 d) | % DE (3 d) |
| Control | 60.78 | 67.87 | 76.35 | 81.97 |
| 0.5x | 27.70 | 73.12 | 80.45 | 96.71 |
| 1x | 22.98 | NA** | 77.01 | NA** |
| 4x | 2.75 | 65.39 | 67.09 | 84.82 |

*immediately, within less than 30 min;
NA: data not available.

Taken together, this degradation profile indicates that the disclosed bone hemostat can effectively maintain its function once applied, and can further be degraded rapidly to prevent the impediment of bone tissue regeneration. Specifically, up to 3 days, more than 80% of the CMS samples were degraded. Thus, for stopping bone bleeding, the practitioner may use the disclosed composition which can be rapidly degraded so that it would not impede the bone regeneration.

Example 5 Hemostatic Efficacy—Animal Study

Methods:

To evaluate the hemostatic efficacy of the PEG400 contained CMS-CA (PEG400/CMS-CA=1:2.7 ratio by weight, which does not adhere to gloves, was chosen; cross-linking ratio was 0.4x; PEG400/glycerol ratio: 2.2:1, by weight), an animal study was performed using sheep ilium defect model. Briefly, defects have been made on sheep ilium.

On each defect surface, the CMS-CA hemostat and one of the control samples were applied simultaneously.

In exemplary procedures, the hemostatic efficacy was evaluated immediately and 10 min post application. The defect was created, and no treatment was applied during 10 min to ensure the hemostasis was not due to auto coagulation. Next, one of the control samples (Bone wax and Ostene (purchased from Baxter)) and CMS-CA or HA-CA were applied to the same defect surface. Acute hemostasis, durable hemostasis and adhesiveness were evaluated.

The detailed procedure is described below.

In a first set of exemplary procedures, the samples were evaluated in an in vivo sheep model both before and after heparin administration. Evaluations in the non-heparinized sheep model were aimed to simulate use of bone hemostats during standard surgery (e.g., spinal surgery). Evaluations in the heparinized sheep model were aimed to mimic the use of bone hemostats in anticoagulated cardiovascular patients (e.g., sternotomy). The target was to apply each of the eight sample (six tests and two controls) a minimum of five times in a non-heparinized animal model and five times in a heparinized animal model. Both non-heparinized and heparinized testing were conducted in each animal. The actual number of applications per sample were determined by the number of accessible application sites available in the six animals included in the study.

Each sheep had four to six defects created on each ilium (mean of five defects per ilium). Each bone section was divided into two testing areas (lateral & medial). Therefore, with right and left ilia there were a total of from eighteen to twenty-two treatment application sites available per animal. Test and control sample applications were randomized in blocks. Treatment blocks were not designed to be completed in a single animal. When a block was not completed in an animal due to inability to create additional defects, it was picked up again in the following animal. Two animals were evaluated per day. The first animal anesthetized each day was assigned treatments from blocks 1-5. The second animal anesthetized each day was assigned treatments from blocks 6-10.

Following defect creation, bleeding intensity was rated by the surgeon as mild, moderate or severe prior to product application. The approximate time required to complete product application was also documented for each application site, and subjective comments regarding usability were captured.

Each application was evaluated for the following endpoints as applicable:

Primary Endpoint Hemostasis: The product's ability to provide hemostasis at the time of completed application was documented. If the product was not hemostatic at the time of completed application, the quality of the persistent bleeding was rated or described. The site was observed for a minimum of 2 minutes and up to 10 minutes post-application to determine whether the bleeding persisted.

Secondary Endpoint Durable Hemostasis: For sites where the primary endpoint was successful, the product's ability to continue to provide hemostasis for a 10-minute period of observation was documented. If bleeding was observed at any time during the 10-minute observation period, the time that bleeding was detected was recorded. Observation of the site was continued for a minimum of 2 minutes or up to the 10-minute endpoint to document whether the breakthrough bleeding persisted.

Additional Endpoints: For sites where the secondary endpoint confirmed successful persistent/durable hemostasis for the 10-minute observation period: failure or persistence of hemostasis with and following suction and lavage was documented and product flammability was evaluated by directly exposing the treatment site to electrocautery.

The exception were two sham treatments performed in the first animal for which the full defect surfaces were used to confirm model performance with and without heparin. Those two sites were subsequently divided into testing areas each for test/control evaluation since bleeding remained consistent throughout the 10-minute sham treatment observation period both with and without heparin anticoagulation.

Model Justification: bone defects created in the wing of the ilium of sheep have been evaluated and found to be an appropriate model for clinically relevant actively oozing bone bleeding. The model allows for multiple bone defects per animal and for sequential bone sectioning allowing for repeated application of the products being investigated. In addition, the exposed bleeding surface is wide enough to allow for side by side application of two different products for simultaneous evaluation. Table 8 summarizes some method parameters.

TABLE 8

| Method Parameters in the Test System | |
| --- | --- |
| Species: | Sheep |
| Strain: | Dorset Cross |
| Gender: | Female or Male |
| Age: | 1-5 years |
| Weight: | 73-95 kg |
| Number: | 6 |

Sample Preparation: Test Sample—The test samples were applied as received. The samples were applied manually, Control Article—Bone Wax was prepared by its warming to the desired consistency using gloved hands/fingers to manipulate to the appropriate shape. The softened sample was then applied to the bone defect.

Procedure: For each ilium, a curvilinear skin incision was made centered over the coaxial tuberosity. Additional bone exposure was established by severing muscle attachments to the wing of the ilium to maximize the sites available for testing. During the procedure, clamps, ligation, electrocautery or appropriate hemostatic agents were used to control soft tissue bleeding as needed prior to bone bleeding evaluations.

Defect/Bleeding Site Creation: The wing of the ilium was serially transected with an osteotome or chisel to create multiple defects. Each defect was divided into two areas for testing (lateral and medial). Testing was performed on both sides. Adjacent product applications overlapped slightly at the midpoint of the testing surface. Any bleeding detected at the overlap point was noted in the comments section but was not attributed to either product. An effort was made to elevate and/or cauterize the periosteum adjacent to the defect sites to minimize interference with subsequent evaluation of bone bleeding from the cancellous bone.

Heparinization of Animals: Intravenous heparin was used to mimic use of bone hemostats in anticoagulated cardiovascular patients. Animals received systemic heparin anticoagulation therapy to enhance bleeding only after both iliac crest soft tissue approaches were complete. Animals received an initial loading intravenous bolus of heparin sodium at 300 IU/kg. Baseline and post-treatment activated clotting time (ACT) were monitored to adjust the dose of heparin used in the animal A minimum of 10 minutes after the initial administration of heparin, a blood sample was drawn, and ACT measured. The animal was appropriately heparinized when ACT was greater than 2 times the baseline reading. Once heparinization was achieved, ACT was performed approximately every 60 minutes to monitor levels and additional boluses administered as necessary. Table 9 presents the bleeding score.

TABLE 9

| Bleeding Score | |
|---|---|
| Score | Description |
| Mild | Small amount of blood oozing at the defect |
| Moderate | Moderate amount of blood oozing at the defect |
| Severe | Significant amount of blood oozing at the defect |

Sham Treatment Sites: A sham application was performed as the first treatment site for one animal (the first animal in the study) in the non-heparinized and heparinized state to confirm the bleeding model for this study. For these sham applications, the bone surface was exposed and observed for persistent bleeding over a 10-minute observation period with periodic application of gauze tamponade to allow adequate evaluation of bleeding at that site. At the beginning and the end of the observation period, a bleeding score was assigned as in Table 9. After the observations were completed the sham sites were used for the first pair of product applications since bleeding remained consistent during the 10-minute observation period.

Test and Control article treatment sites: the first side of the pelvis exposed for each animal was used for non-heparinized testing, and then after the second side of the pelvis was exposed the animal was heparinized and the remaining anticoagulated testing was complete. Both the Study Director and the Surgeon performed evaluations and made associated comments.

For test and control sample treated sites, the article was applied to the bleeding defect sites in a single application with an amount of article that the surgeon considered appropriate to provide hemostasis. Sample was applied to both the lateral and medial surfaces of the defect. The samples overlapped at the midpoint of the defect sites. The following information about Test and Control article handling and application was documented:

1. The mass of product applied by weight.
2. Time required for complete product application.
3. Handling of the test article prototypes was subjectively compared to bone wax. Surgeon comments regarding handling characteristic were captured.

Test and control article hemostatic efficacy were evaluated for up to 10 minutes following application. The evaluator differentiated bleeding from the cancellous bone from that produced by the adjacent periosteum. Periosteal bleeding cannot be expected to be controlled by bone hemostat application.

The following endpoints were evaluated:

1. Primary hemostasis—Did the product control bleeding at the time of completed application ('Yes' or 'No').
   a. If 'Yes'—Move to endpoint 2
   b. If 'No'—Document the time to failure and score the bleeding per Table 9. Continue to observe site for at least 2 minutes, and note any time to delayed hemostasis before terminating testing for test site. If delayed hemostasis was achieved within 2
   c. minutes, move to 2. If delayed hemostasis was not achieved within 2 minutes, terminate testing.
      i. Document whether the evaluator felt that they had adequately applied the product.
2. Secondary Durable Hemostasis—Does the product control bleeding for a full 10-minute observation period ('Yes' or 'No')
   a. If 'Yes'—move to endpoint 3
   b. If 'No'—score the bleeding as in Table 9, terminate formal testing or the evaluator may elect to observe and record comments for an additional 2 minutes or out to the end of the 10-minute observation period (whichever comes first).
3. Subordinate success criteria—Only applied to those test sites that were hemostatic for 10 minutes.
   a. Following the 10-minute observation period, did the product adhere under lavage and suction applied directly to the site? ('Yes' or 'No')
      i. If 'Yes'—move to c
      ii. If 'No'—move to b
   b. Did the site remain hemostatic for 2 minutes after the product lifts away? ('Yes' or 'No'). If 'No', score the bleeding as in Table 1.
   c. Did the product show evidence of flammability when exposed to direct electrocautery? ('Yes' or 'No').
      i. The electrocautery unit identification and power settings were documented.

FIGS. 6A-B present photographic images illustrating the hemostasis evaluation on sheep ilium defect model: the defect was created, and no treatment was applied during 10 min to ensure the hemostasis was not due to auto coagulation (FIG. 6A) and when Bone wax and CMS-CA were applied to the same defect surface (FIG. 6B). Acute hemostasis, durable hemostasis and adhesiveness were evaluated.

Table 10 presents combined result of hemostasis and adhesiveness. The test article and bone wax were evaluated for hemostasis and bone adhesiveness, under non-heparinized and heparinized condition, respectively. Hemostatic efficacy was evaluated at 0 mm and 10 min post application. The bone adhesiveness was investigated afterward with saline irrigation.

TABLE 10

| | End Point results-Sheep Model | | | | | | | |
|---|---|---|---|---|---|---|---|---|
| | Application Time | | Primary Hemostasis | | Durable Hemostasis | | Adherence during Lavage and Suction | |
| Sample | heparin | non-heparin | heparin | non-heparin | heparin | non-heparin | heparin | non-heparin |
| Bone wax (Baxter) | 8.75s | 6.4s | 5/5 | 5/5 | 5/5 | 5/5 | 4/5 | 5/5 |
| CMS-CA | 17.0s | 10.8s | 3/5 | 3/5 | 2/5 | 4/5 | 2/5 | 3/5 |
| HA-CA* | 27.0s | 15.6s | 5/5 | 4/5 | 4/5 | 5/5 | 4/5 | 5/5 |

TABLE 10-continued

| | End Point results-Sheep Model | | | | | | | |
|---|---|---|---|---|---|---|---|---|
| | Application Time | | Primary Hemostasis | | Durable Hemostasis | | Adherence during Lavage and Suction | |
| Sample | heparin | non-heparin | heparin | non-heparin | heparin | non-heparin | heparin | non-heparin |
| Ostene (Baxter) | 8.6s | 4.0s | 5/5 | 5/5 | 4/5 | 4/5 | 5/5 | 5/5 |

*Unless stated otherwise in this Example "HA-CA" refers to HA-CA 0.5X, PEG400 to glycerol 1:2.2 In additional exemplary experiments, crosslinked hyaluronic acid (HA) (Shanghai Macklin Biochemical Co. Ltd) paste and CMS were compared for hemostatic efficacy. These two prototypes were evaluated on sheep model.

Table 11 presents comparative results of primary hemostasis for Bone wax, Ostene (Baxter) HA-CA and CMS-CA.

TABLE 11

| | Primary Hemostasis | | | | | |
|---|---|---|---|---|---|---|
| Article | Replicates performed combined heparinized and non-heparinized | Ratio % hemostatic (for combined) | Replicates performed non-heparinized | % Hemostatic (for non-heparinized) | Replicates performed heparinized | % Hemostatic (for non-heparinized) |
| Bone wax | 10 | 100 | 5 | 100 | 5 | 100 |
| CMS-CA | 10 | 60 | 5 | 60 | 5 | 60 |
| HA-CA | 10 | 90 | 5 | 80 | 5 | 100 |
| Ostene | 10 | 100 | 5 | 100 | 5 | 100 |

Table 12 presents comparative results of durable hemostasis for Bone wax, Ostene (Baxter) HA-CA and CMS-CA.

TABLE 12

| | Durable hemostasis | | | | | |
|---|---|---|---|---|---|---|
| Article | Replicates performed-combined heparinized and non-heparinized | Ratio % hemostatic (for the combined) | Replicates performed-non-heparinized | % Hemostatic (for non-heparinized) | Replicates performed-heparinized | % Hemostatic (for heparinized |
| Bone wax | 10 | 100 | 5 | 100 | 5 | 100 |
| CMS-CA | 10 | 60 | 5 | 80 | 5 | 40 |
| HA-CA | 10 | 90 | 5 | 100 | 5 | 80 |
| Ostene | 10 | 80 | 5 | 80 | 5 | 80 |

50

Table 13 presents comparative results of adherence for Bone wax, Ostene (Baxter) HA-CA and CMS-CA.

TABLE 13

| | Comparative results of adherence | | | | | |
|---|---|---|---|---|---|---|
| Article | Replicates evaluated for irrigation and lavage combined heparinized and non-heparinized | % Adherent irrigation and suction (combined) | Replicates performed non-heparinized | % Adherent with irrigation and suction (non-heparinized) | Replicates performed heparinized | % adherent with irrigation and suction (heparinized) |
| Bone wax | 10 | 90 | 5 | 100 | 5 | 80 |
| CMS-CA | 10 | 50 | 5 | 60 | 5 | 40 |

TABLE 13-continued

| | Comparative results of adherence | | | | | |
|---|---|---|---|---|---|---|
| Article | Replicates evaluated for irrigation and lavage combined heparinized and non-heparinized | % Adherent irrigation and suction (combined) | Replicates performed non-heparinized | % Adherent with irrigation and suction (non-heparinized) | Replicates performed heparinized | % adherent with irrigation and suction (heparinized) |
| HA-CA | 10 | 90 | 5 | 100 | 5 | 80 |
| Ostene | 10 | 100 | 5 | 100 | 5 | 100 |

Table 14 presents cumulative performance initial+durable hemostasis+adherence results of adherence for Bone wax, Ostene (Baxter) HA-CA and CMS-CA.

TABLE 14

| | Cumulative performance | | |
|---|---|---|---|
| Article | Replicates performed combined heparinized and non-heparinized | Replicates performed both immediately and durably hemostatic, and adherent with irrigation and suction | % Immediately and durably hemostatic and adherent with irrigation and suction |
| Bone wax | 10 | 10 | 90 |
| CMS-CA | 10 | 6 | 83 |
| HA-CA | 10 | 9 | 100 |
| Ostene | 10 | 8 | 100 |

Table 15 presents hemostasis following irrigation and suction (either adherent or non-adherent but with no evidence of subsequent rebleeding).

TABLE 15

| | Hemostasis following irrigation and suction | | | | | |
|---|---|---|---|---|---|---|
| Article | Replicates evaluated for irrigation and lavage combined heparinized and non-heparinized | % Hemostatic with irrigation and suction | Replicates performed non-heparinized | % Hemostatic with irrigation and suction (non-heparinized) | Replicates performed heparinized | % Hemostatic with irrigation and suction (heparinized) |
| "1" Bone wax | 10 | 90 | 5 | 100 | 5 | 80 |
| "3" CMS-CA | 6 | 83 | 4 | 75 | 2 | 100 |
| "4" HA-CA | 9 | 100 | 5 | 100 | 4 | 100 |
| '5" Ostene | 8 | 100 | 4 | 100 | 4 | 100 |

FIG. 7 presents combined result of hemostasis for CMS-CA, and control (bone wax from Baxter), based on Table 15 demonstrating that the CMS-CA provides similar hemostasis performance compared to bone wax.

Table 16 presents cumulative performance final hemostasis score considering all evaluations.

TABLE 16

| | Cumulative performance: Final hemostasis score | | |
|---|---|---|---|
| Article | Replicates performed in study combined heparinized and non-heparinized | Replicates that maintain hemostasis throughout all phases of evaluation | % Hemostasis (maintained hemostasis throughout all phases of evaluation) |
| Bone wax | 10 | 9 | 90 |
| CMS-CA | 10 | 5 | 50 |
| HA-CA | 10 | 9 | 90 |
| Ostene | 10 | 8 | 80 |

Thus, it can be concluded that both HA-CA and CMS-CA samples can stop bleeding, as tested in the defect model.

The HA-CA sample seems even more effective on hemostasis than CMS-CA sample. However, the degradation profile of HA sample is slower than that of CMS.

When evaluating the efficacy of the tested samples in a porcine femur cross-section model, non-absorbable, tough appearance of the wax, and weak adhesiveness of Ostene were demonstrated.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A non-flowable and deformable hemostatic composition comprising: a xerogel crosslinked powdered polysaccharide dispersed within a substantially anhydrous blend of: glycerol, and polyethylene glycol (PEG), wherein said PEG and glycerol are present in a ratio ranging from higher than 1:1.3: to below 1:2.7, by weight, respectively, and wherein the powder content in the composition is above 50%, by weight.

2. The composition of claim 1, wherein the polysaccharide comprises a polymer selected from the group consisting of: carboxymethyl starch (CMS), cross-linked hyaluronate (HA), and a mixture or a copolymer thereof.

3. The composition of claim 1 or 2, wherein the PEG comprises PEG 400.

4. The composition of claim 1, wherein the xerogel crosslinked powdered polysaccharide is milled.

5. The composition of claim 1, wherein the crosslinked polysaccharide is crosslinked via a polyfunctional carboxylic acid, wherein said acid is selected from the group consisting of: malic acid, tartaric acid, citric acid, malonic acid, succinic acid, glutaric acid, adipic acid, and any mixture or combination thereof.

6. The composition of claim 5, wherein said acid comprises citric acid.

7. The composition of claim 1, wherein said xerogel crosslinked powdered polysaccharide is in the form of suspended powder having median particle size of less than 100 microns.

8. The composition of claim 1, comprising less than 3% of water.

9. The composition of claim 1, wherein the glycerol is present at a concentration of 15 to 30%, and the PEG is present at a concentration of 10 to 25%, by weight.

10. The composition of claim 1, wherein the xerogel crosslinked powdered polysaccharide has a swelling capacity in water of at least 10 times, by weight, at 25° C. within less than 2 min.

11. The composition of claim 1, wherein the xerogel crosslinked powdered polysaccharide features a degradation rate of 60% to 80%, by initial weight, in vivo.

12. The composition of claim 1, being substantially devoid of polypropylene glycol.

13. The composition of claim 1, wherein the powder content in the composition is above 60% by weight.

14. The composition of claim 1, characterized by adhesiveness ranging from 2.5 to 4.5 N/m as measured by T-peel test e.g., according to ASTM F2256-052015.

15. The composition of claim 1, being in the form of paste.

16. The composition of claim 1, characterized as being non sticky to nitrile.

17. The composition of claim 1, having a crosslinking degree ($\rho$) of 0.0047 to 0.0054 mol/ml.

* * * * *